US00PP35253P2

(12) United States Plant Patent
Brenes Angulo

(10) Patent No.: US PP35,253 P2
(45) Date of Patent: Jul. 4, 2023

(54) ***SANSEVIERIA* PLANT NAMED 'PHEASANT TAIL'**

(50) Latin Name: *Sansevieria trisfaciata*
Varietal Denomination: Pheasant Tail

(71) Applicant: UNIVERSIDAD DE COSTA RICA, San Jose (CR)

(72) Inventor: Arturo Brenes Angulo, San Jose (CR)

(73) Assignee: UNIVERSIDAD DE COSTA RICA, San Jose (CR)

( * ) Notice: Subject to any disclaimer, the term of this patent is extended or adjusted under 35 U.S.C. 154(b) by 0 days.

(21) Appl. No.: 17/535,992

(22) Filed: Nov. 27, 2021

(51) Int. Cl.
*A01H 5/12* (2018.01)
*A01H 6/12* (2018.01)

(52) U.S. Cl.
USPC ..... Plt./382
CPC ..... *A01H 6/12* (2018.05)

(58) Field of Classification Search
USPC ..... Plt./382
CPC ..... A01H 6/12
See application file for complete search history.

*Primary Examiner* — Anne Marie Grunberg
(74) *Attorney, Agent, or Firm* — Jerold I. Schneider; Schneider IP Law

(57) ABSTRACT

The new plant variety 'Pheasant Tail' is part of the long leaves *Sansevieria* varieties. It can reach 90 cm in length, with an average of approximately 4-7 leaves per plant. The new plant variety 'Pheasant Tail' is cylinder shaped, the arrangement of the leaves is in the form of a rosette. Leave colors are very different compared to its parent variety ('Wintergreen'), but like its parent variety the new plant variety 'Pheasant Tail' shows also variegated bands on the leaves with no distinguishable margins and produces more leaves per rosette. Additionally, new plant variety 'Pheasant Tail' shows, unlike the parent variety, high resistance to anthracnose disease caused by *C. sansevierae* which gives the new variety a greater competitive advantage as well as its sister variety 'Spearmint' (U.S. Plant Pat. No. 32,333).

3 Drawing Sheets

Latin name of the genus and species of the claimed plant: *Sansevieria: Sansevieria trisfaciata.*

Plant variety denomination: 'PHEASANT TAIL'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'Pheasant Tail'

*Sansevieria* is a monocotyledonous and succulent, flowering plant which can be produced in either hard-leafed or soft-leafed varieties for interior use as a house plant or outdoors ornamental plant.

The new *Sansevieria* plant variety 'Pheasant Tail', originated from a laboratory induced mutation of the *Sansevieria* 'Wintergreen' covered by U.S. Plant Pat. No. 24,939. The new *Sansevieria* 'Pheasant Tail' was discovered and selected by the inventor, Arturo Brenes Angulo, as a single plant in a group of mutant plants arising from calli of 'Wintergreen' variety, under controlled environment.

In the Plant Biotechnology Laboratory of the Agronomic Research Center of the University of Costa Rica, meristems of the plant variety 'Wintergreen' U.S. Plant Pat. No. 24,939, were established in vitro in Murashige and Skoog (1962) medium, containing Thidiazuron (TDZ) (Sigma-Aldrich) in different concentrations, to induce the formation of calli and shoots.

When shoots reached at least 2 cm in length, they were separated and subcultured in the same medium without TDZ to promote growth and rooting. After 8 weeks, when plantlets were approximately 8 cm long, they were taken to the greenhouse and acclimatized in seedling trays containing peat moss with perlite (TS1, Klasmann-Deilmann GmbH, Germany). After 8 weeks, completely rooted and acclimatized plants were transplanted to 260 m cups containing the same substrate as for acclimatization. Vitroplants were fertilized with complete formula every 8 weeks. When plants were 6 months old, and presented 4 to 6 leaves, they were artificially inoculated with *C. sansevierie*, the causal agent of *Sansevieria anthracnose*, to determine if any of them showed resistance to the disease. From 436 plants inoculated, 234 showed resistance. All of them were taken to the field in Bajo Rodriguez in Alajuela province, to be evaluated and to determine their potential to be developed as a new plant variety. After one year of field evaluation, one of the variants was selected for its phenotypic characteristics and propagated under the same conditions to start the commercial evaluation process.

Asexual reproduction of the new *Sansevieria* plant variety by vegetative cuttings was first performed in January 2019 in Bajo Los Rodriguez, San Ramón, Alajuela, and demonstrated that the combination of characteristics as herein disclosed for the new plant variety are firmly fixed and retained through successive generations of asexual reproduction. The new cultivar reproduces true to type and shows high resistance level to anthracnose disease and its leaves are extremely tough to indoor conditions.

BRIEF SUMMARY OF THE INVENTION

The following traits have been repeatedly observed and are determined to be unique characteristics of the new plant variety 'Pheasant Tail', which in combination distinguish this *Sansevieria* as a new and distinct cultivar:

The new variety 'Pheasant Tail', is considered a variety of *Sansevieria* in the group denominated as "long leaves *Sansevieria* varieties". Presents an average of 4-7 leaves per plant when it reaches its maturity (between 8-10 months). The new plant variety 'Pheasant Tail' shows erect growth habit and the entire plant can reach a high range between 50-90 cm. The leaves are narrow and lanceolated (3-5 cm average measured at the widest part of the mature leaf), with a soft waxy texture and the blades are thin and slightly wavy. The plant has a cylindrical shape and shows colors very different from its parent variety 'Wintergreen' (Patented, U.S. Plant Pat. No. 24,939). Unlike its parent variety 'Pheasant Tail' shows variegated leaves with different banding tones and produces more leaves per rosette.

This variety is moderately drought tolerant, highly resistant to anthracnose disease (*C. sansevierae*) and adapts well to conditions of light and shade (interior and exterior).

The mature leaf blade is deep green colored (RHS 139A) and presents also non- uniform horizontal narrow variegated bands in both sides of the leaves, with RHS 145D coloration.

General traits of 'Pheasant Tail'

1. Deep-green colored foliage and non-uniform narrow pale green bands in the leaf blade.
2. Narrow and lanceolated leaves 50-90 cm long and supported in a rosette.
3. 50-90 cm plant height.
4. Plant habit: Erect.
5. Needs little water and is very drought and anthracnose disease resistant.

Plants of the new *Sansevieria* plant variety 'Pheasant Tail' differ from plants of the parental cultivar, 'Wintergreen' (patented, U.S. Plant Pat. No. 24,939), in the characteristics described in Table 1.

The variety 'Wintergreen' gave rise to the variety 'Pheasant Tail' through a mutagenesis process. The 'Pheasant Tail' variety is also considered into the "Long leaves varieties" group. Shows more vigor than 'Wintergreen', higher number of leaves per plant (5-7), with an average width of 3-5 cm (measured in the middle of the mature leaf). The growth habit is erect and presents narrow leaves supported in a rosette. The entire plant can reach a size between 50-90 cm, The plant shows, as for 'Wintergreen', a cylindrical shape. The leaves are lanceolated with a soft, waxy texture. The younger leaves show a green vivid coloration (RHS 143A) in the upper surface of the leaf blade with irregular streaks or narrow pale-green bands (RHS 149C). In the lower surface, irregular horizontal bands alternate between green (RHS 144A) and broad pale green bands (RHS 142D). Irrespectively of the maturity, leaves do not show any remarkable margins.

Plants of the new *Sansevieria* 'Pheasant Tail' differ from plants of the parental cultivar, 'Wintergreen' (patented) in the characteristics described in Table 1.

TABLE 1

Comparison between the new plant variety with its parent variety 'Wintergreen' and its sister variety 'Spearmint'

| Characteristic | New plant variety 'Pheasant Tail' | Parent variety 'Wintergreen' |
|---|---|---|
| Plant Vigor | More vigorous (more leaves)* | Less vigorous (less leaves) |
| Color | Variegated leaves with medium pale green and non-uniform narrow cross-banding with non distinguishable margins. | variegated leaves with wide light yellowish green cross-banding and green margins |
| Shape | Narrow and lanceolated leaves on a rosette | narrow and lanceolated leaves on a rosette |
| Texture of leaves | smooth-textured leaves | smooth-textured leaves |
| Anthracnose disease | Highly resistant | Susceptible |

TABLE 1-continued

Comparison between the new plant variety with its parent variety 'Wintergreen' and its sister variety 'Spearmint'

| Characteristic | Sister variety 'Spearmint' (patented) |
|---|---|
| Plant Vigor | Less vigorous (less leaves) |
| Color | Variegated green leaves, greyed-green leaves with irregular thin dark green horizontal bands and green margins |
| Shape | Narrow and lanceolated leaves on a rosette |
| Texture of leaves | smooth-textured leaves |
| Anthracnose disease | Susceptible |

*= With regard to vigor, in this case it refers to the fact that the shoots that are marketed, only produce two leaves in the case of 'Wintergreen', while the 'Pheasant Tail' produces 3 leaves, which reduces costs, since in the case of the var. 'Wintergreen' two shoots must be put together to be sold as a unit.

Of the many commercial cultivars known to the present inventor, the most similar in comparison to the new *Sansevieria* 'Pheasant Tail' is the *Sansevieria* 'Wintergreen' (patented), however, unlike the 'Wintergreen', 'Pheasant Tail' variety shows high resistance to anthracnose disease which gives it competitiveness were other *Sansevieria* varieties fail. Plants of the new variety 'Pheasant Tail' can also be compared to the commercial variety *Sansvieria* 'Spearmint' (patented), which also came from the plant variety 'Wintergreen' (patented).

Plants of the new variety differ in the following characteristics:

1. Foliage of the new variety is more vigorous
2. Leaves show medium pale green and non-uniform narrow cross-banding with non-distinguishable margins.
3. The new variety shows high resistance to anthracnose disease.

BRIEF DESCRIPTION OF THE PHOTOGRAPHS

The accompanying photographs illustrate the overall appearance of the new *Sansevieria* plant variety 'Pheasant Tail' showing the colors as true as is reasonably possible with colored reproductions of this type. Colors in the photographs may differ slightly from the color value cited in the detailed botanical description which accurately describe the color of 'Pheasant Tail'.

DETAILED BOTANICAL DESCRIPTION

Figure 1:
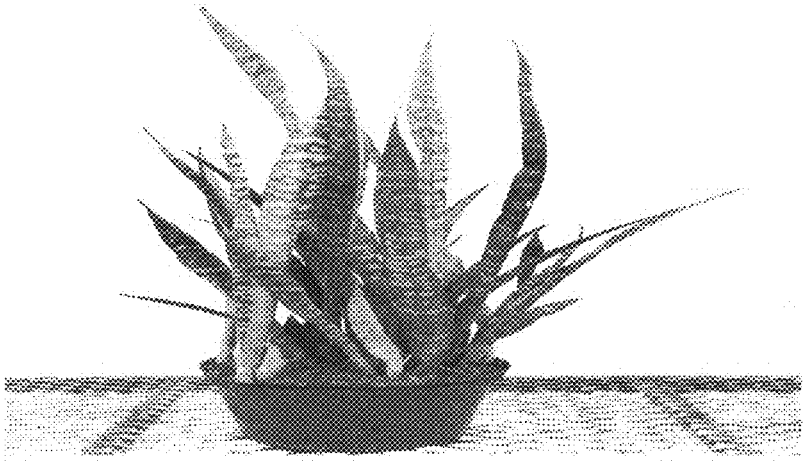
FIG. 1 Shows a nine-month-old plant of *Sansevieria* 'Pheasant Tail' in a 21 cm diameter pot (Side view).
Figure 2:
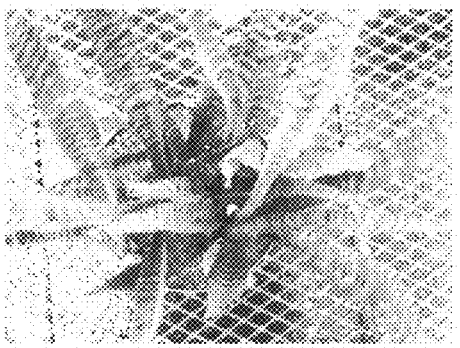
FIG. 2 Shows a nine-month-old plant of *Sansevieria* 'Pheasant Tail' in a 21 cm diameter pot (Top view).
Figure 3:
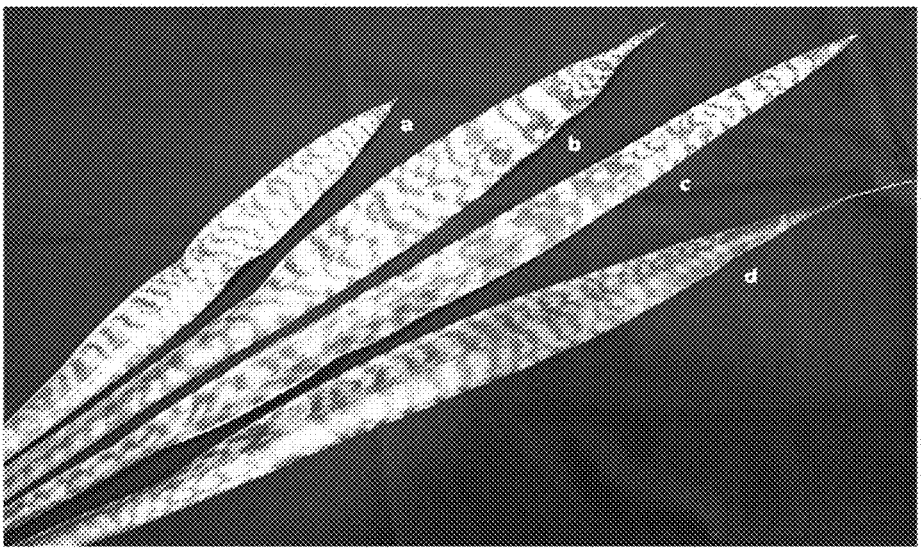
FIG. 3 Shows a close-up view of the typical leaves of 'Pheasant Tail' from an Nine-month old plant. upper side. (a), very young leaf, (b and c), intermediate young leaves and (d), completely mature leave.
Figure 4:
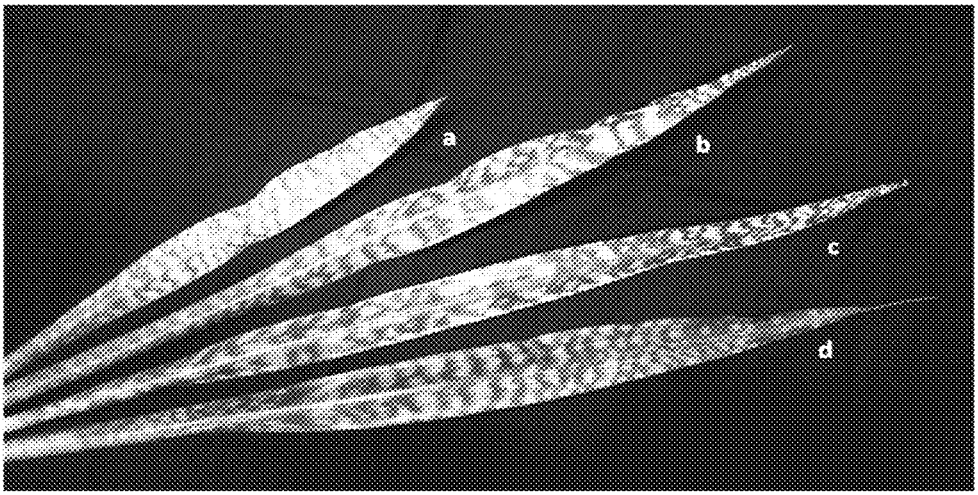
FIG. 4 Shows a close-up view of the typical leaves of 'Pheasant Tail' from a Nine-month old plant, under side. (a), very young leaf, (b and c), intermediate young leaves and (d), completely mature leave.
Figure 5:
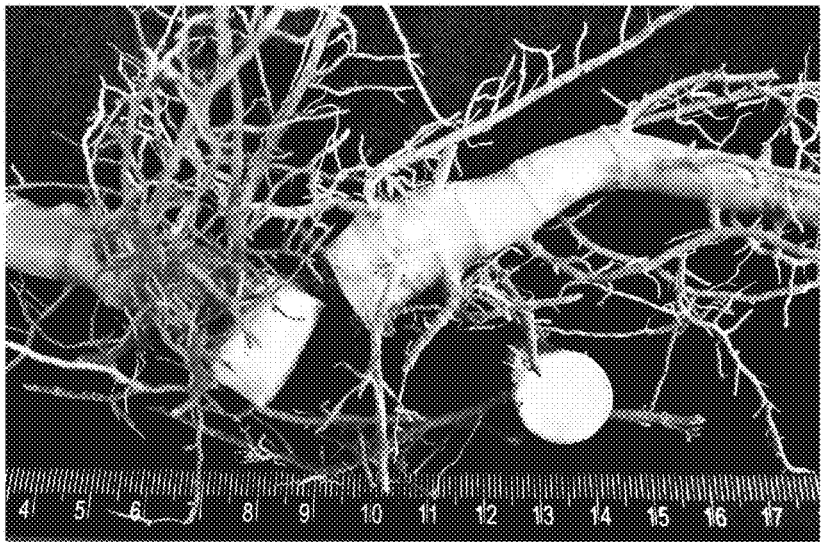
FIG. 5 Shows a view of the rhizome of 'Pheasant Tail' from a Nine-month-old plant grown in a 21 cm diameter pot.

The new *Sansevieria* plant variety 'Pheasant Tail' has not been observed under all possible environmental conditions. The new cultivar may shows phenotypic changes with variations in environment such as temperature, light intensity, and day length without any change in the genotype of the plant.

The photographs, together with the following observations, measurements and values describe the new *Sansevieria* Tail" plant variety 'Pheasant Tail' as grown in open-field conditions at Bajo Los Rodriguez, San Ramón, Alajuela province, Costa Rica, which closely approximate those generally used in commercial practice. Average temperature at Bajo Los Rodriguez. is 26 ° C. during the day and 18° C. at night. Plants grow under natural light conditions.

This crop does not require constant fertilization, however, to increase production per area about 200 kg ha-1 N, 150 kg ha-1 of P and 100 kg ha-1 K are required, the production is closely related with soil conditions in which they are grown.

Color references were made according to The Royal Horticultural Society Colour Chart (R.H.S., April 2009). The photographs and descriptions were made during the rainy season in Bajo Los Rodriguez, San Ramón, Alajuela province, Costa Rica when outdoor day average temperature was 26° C. The age of the plants described is 9 months.

Classification:

*Botanical.*—*Sansevieria trifasciata.*

*Variety denomination.*—'Pheasant Tail'.

Parentage: *Sansevieria trifasciata*, 'Wintergreen' (patented).

Optimal growth conditions:

*Light intensities.*—High adaptability to outdoor or indoor conditions.

*Temperature.*—Day: 26° C. to32° C. Night: 18° C. to 23° C.

*Temperature tolerance.*—Tolerant to temperatures between 12° C. and 35° C.

*Fertilization.*—200, 150 and 100 kg ha-1 of N, P and K.

*Growth regulators.*—Not necessary.

Propagation:

*Type.*—Vegetative, by rooted cuttings.

*Rooting habit description.*—Rizomes, with short roots.

*Time to initiate roots.*—15 to 22 days at 20-25° C.

*Faster time to produce a rooted cutting.*—About 60 to 90 days at 20-25° C.

Plant:

*General appearance and form.*—

*Height.*—About 90 cm when grown on the ground; About 90 cm when grown in a 21 cm size container.

*Spread.*—About 15 cm when grown on the ground or in 21 cm size container.

*Form.*—Monocot; leaf bases arranged in a rosette around growing point.

*Shape.*—Cylindrical.

*Growth rate and habit.*—About 2.5 cm per week; upright.

*Fragrance.*—None.

*Stem.*—Modified (Rhizome and foliage).

*Length.*—About 20 cm when grown in ground. About 15 cm when grown in 21 cm size container.

*Diameter.*—About 2.0 cm.

*Shape.*—Round.

*Texture.*—Rough.

*Color.*—RHS 25C.

*Strength.*—Strong and durable.

*Internode length.*—Between 15 mm to 17 mm.

Foliage:

*Quantity.*—About 4-7 leaves in a mature single plant.

*Arrangement and attachment.*—Single, alternate; leaf bases arranged in a rosette around growing point.

*Leaf length.*—About 90 cm.

*Leaf width.*—About 4-5 cm.

*Overall shape of leaf.*—Lanceolated.

*Apex shape.*—Acute, triangular.

*Base shape.*—Plane.

*Margin.*—Sharp, smooth.

*Texture.*—Upper Surface: smooth and waxy texture. Under Surface: smooth and waxy texture.

*Pubescence.*—None. Upper Surface: Lower Surface:

*Color of mature leaf.*—Upper Surface: RHS 139A, 145D. Lower Surface: RHS 139A, 145D.

*Color of immature leaf.*—Upper Surface: RHS 143A, 149C. Lower Surface: RHS 144A, 142D.

*Venation.*—Pattern: longitudinal/parallel leaf shape. Color: None. Leaf fragrance: None.

Inflorescence description: Not observed so far.

Weather resistance: Drought tolerant.

Disease/pest resistance: Highly resistant to anthracnose (*C. sansevierae*).

Disease/pest susceptibility: not observed so far.

I claim:

1. A new and distinct variety of *Sansevieria* plant named 'Pheasant Tail' substantially as illustrated and described herein.

* * * * *